United States Patent
O'dea

(10) Patent No.: US 8,701,664 B2
(45) Date of Patent: *Apr. 22, 2014

(54) APPARATUS AND METHOD FOR RELIEVING DYSPNOEA

(75) Inventor: John O'dea, Galway (IE)

(73) Assignee: Caradyne (R&D) Limited, Galway (IE)

( * ) Notice: Subject to any disclaimer, the term of this patent is extended or adjusted under 35 U.S.C. 154(b) by 2143 days.

This patent is subject to a terminal disclaimer.

(21) Appl. No.: 10/796,585

(22) Filed: Mar. 9, 2004

(65) Prior Publication Data

US 2005/0034724 A1 Feb. 17, 2005

Related U.S. Application Data

(63) Continuation-in-part of application No. 09/831,388, filed as application No. PCT/IE99/00112 on Nov. 8, 1999, now Pat. No. 6,705,314.

(30) Foreign Application Priority Data

Nov. 6, 1998 (IE) ........................ S980914

(51) Int. Cl.
*A61M 16/00* (2006.01)

(52) U.S. Cl.
USPC ............ 128/204.23; 128/204.18; 128/204.21; 128/204.22; 128/204.26

(58) Field of Classification Search
USPC .............. 128/204.18, 204.21–204.23, 204.26
See application file for complete search history.

(56) References Cited

U.S. PATENT DOCUMENTS

| | | | | |
|---|---|---|---|---|
| 4,057,059 A | * | 11/1977 | Reid et al. ................ | 128/204.24 |
| 4,079,735 A | | 3/1978 | Gaffney | |
| 4,082,093 A | * | 4/1978 | Fry et al. .................. | 128/204.25 |
| 4,444,201 A | * | 4/1984 | Itoh ............... | 600/529 |
| 4,773,411 A | | 9/1988 | Downs | |
| 4,807,616 A | * | 2/1989 | Adahan .................... | 128/204.21 |
| 5,134,995 A | * | 8/1992 | Gruenke et al. ......... | 128/204.23 |
| 5,507,282 A | * | 4/1996 | Younes .................... | 128/204.21 |
| 5,551,419 A | * | 9/1996 | Froehlich et al. ........ | 128/204.23 |
| 5,657,752 A | | 8/1997 | Landis et al. | |
| 5,660,170 A | * | 8/1997 | Rajan et al. .............. | 128/204.18 |
| 5,664,562 A | | 9/1997 | Bourdon | |
| 5,752,509 A | | 5/1998 | Lachmann et al. | |
| 5,868,133 A | * | 2/1999 | DeVries et al. .......... | 128/204.21 |
| 6,099,481 A | * | 8/2000 | Daniels et al. ............... | 600/538 |
| 6,484,719 B1 | | 11/2002 | Berthon-Jones | |
| 6,705,314 B1 | * | 3/2004 | O'Dea ..................... | 128/204.18 |

FOREIGN PATENT DOCUMENTS

| | | |
|---|---|---|
| EP | 0 549 299 A2 | 6/1993 |
| FR | 2 695 830 | 9/1992 |
| WO | WO 96/11717 | 4/1996 |
| WO | WO 98/12965 | 4/1998 |

\* cited by examiner

*Primary Examiner* — Melanie Tyson
*Assistant Examiner* — Katelyn Bernier
(74) *Attorney, Agent, or Firm* — Michael W. Haas

(57) ABSTRACT

Apparatus (1) for relieving dyspnoea in an ambulatory exercising subject comprises a housing (3) to be worn on the subject, and within which a variable speed air blower motor (5) is located for delivering an air supply to the subject through a mouthpiece (10) at a pressure similar to average intrinsic positive end-expiratory pressure of the subject. A pressure transducer (25) in the mouthpiece (10) monitors the pressure during breathing cycles of the subject, and a control circuit (22) determines the average intrinsic positive end-expiratory pressure of the subject over five breathing cycles. The control circuit (22) operates the air blower motor (5) for delivering the air supply to the subject at a pressure similar to the determined average intrinsic positive end-expiratory pressure.

11 Claims, 4 Drawing Sheets

Figure 6:
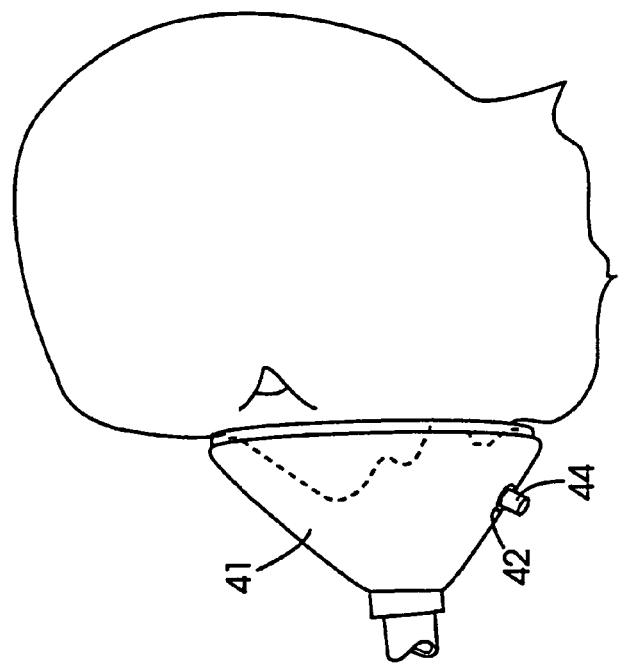

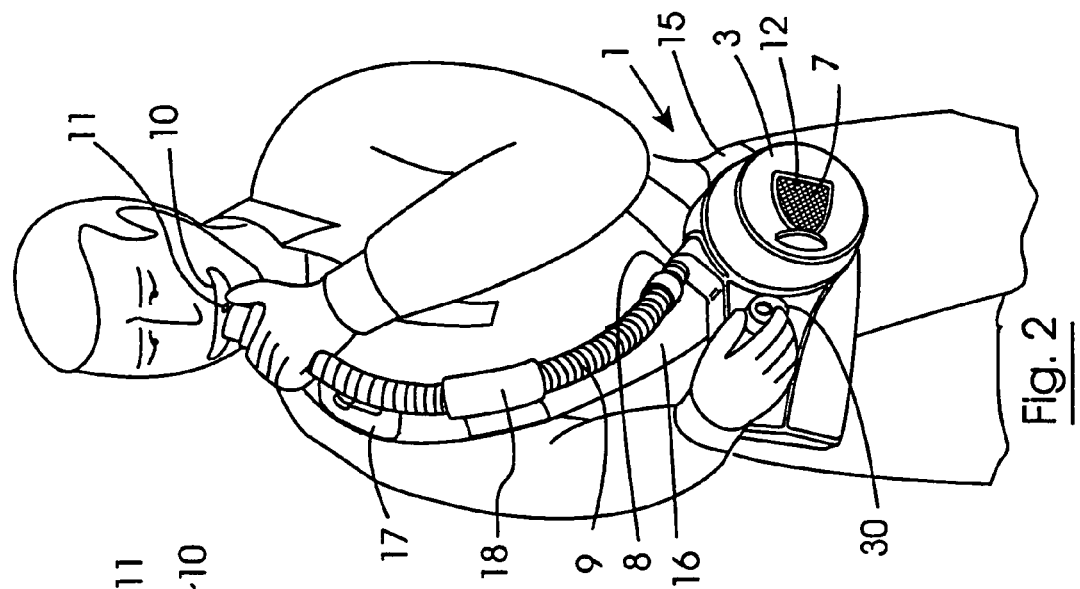
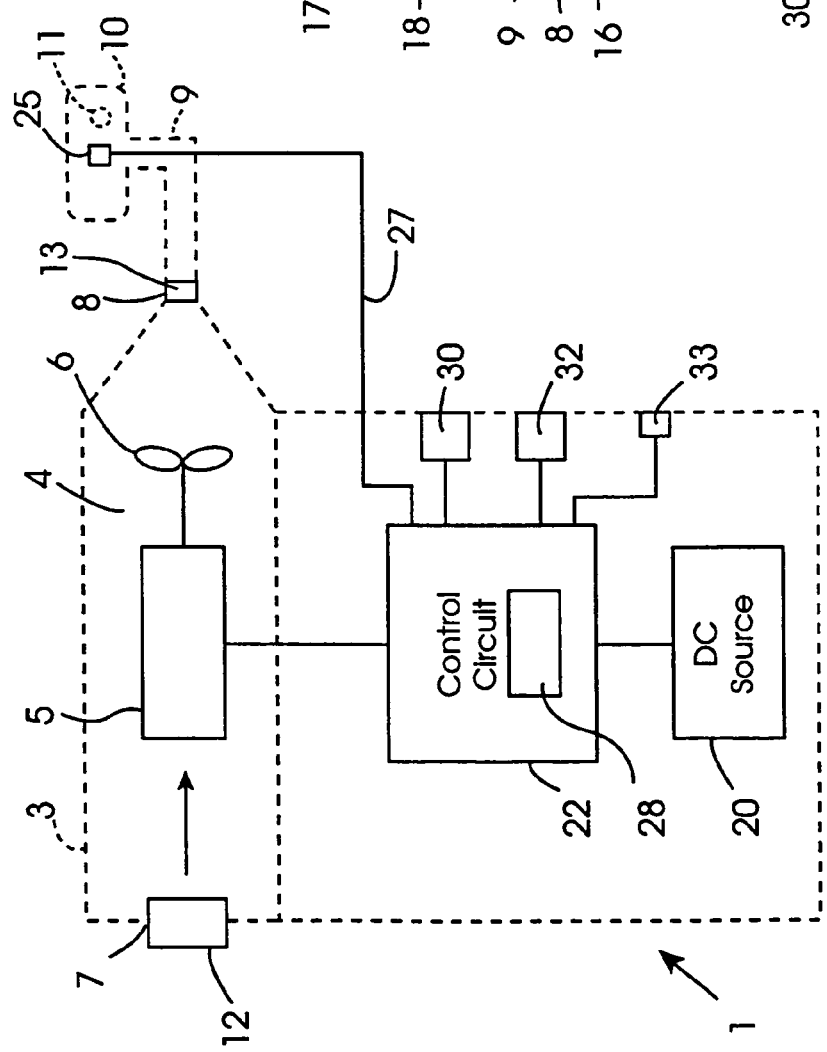
Fig. 2
Fig. 3

APPARATUS AND METHOD FOR RELIEVING DYSPNOEA

This application is a continuation of U.S. patent application Ser. No. 09/831,388, filed Aug. 10, 2001, entitled "Apparatus and a Method for Relieving Dyspnoea," which was a 35 U.S.C. §371 national phase of PCT/IE99/00112, filed on Nov. 8, 1999, which claims priority to Irish Application Serial No. S980914, filed Nov. 6, 1998.

The present invention relates to apparatus and method for relieving dyspnoea, and in particular, though not limited to apparatus and method for relieving dyspnoea in an ambulatory subject, and more particularly, through not limited to an exercising ambulatory subject.

Subjects who suffer from respiratory disorders such as chronic obstructive pulmonary disease often suffer from dyspnoea or breathlessness. This is particularly so in exercising subjects. The term "exercising" is used in this specification, in general, to include activities beyond the resting state, for example, the act of walking, ascending a stairs, or the like. Dyspnoea and the fear of a spell of dyspnoea create great anxiety in such subjects, and can severely limit their ability to perform even the most simple tasks, such as walking a relatively short distance, or ascending a stairs within a house. Apparatus for relieving dyspnoea in ambulatory subjects are known, although they suffer from limitations. Typically, such apparatus are portable and may be worn or carried by the subject. Typically, they provide a supply of air to a mouthpiece, a nasal mask or a face mask to be worn by the subject, and the air pressure is at a pressure greater than ambient pressure. In general, a housing which houses a blower motor is worn or carried by the subject, and a communicating conduit delivers air from the blower motor to the mouth piece or mask at the pressure greater than ambient. Typically, a controller is provided within the housing for controlling the air blower for varying the pressure at which the air is supplied to the mouthpiece for the subject. A control knob on the housing facilitates selection by the subject of the pressure at which the air is to be supplied, similarly controlled non-portable apparatus are also known.

While such apparatus are satisfactory for a subject who, for example, is resting, or alternatively is exercising at a relatively constant rate by, for example, walking at a constant rate, they are unsatisfactory where the rate of exercising by the subject is varying, for example, in the case of a subject walking from a downstairs room to an upstairs room in a house. While the subject is walking on level ground the exercise rate is at one level, however, when ascending the stairs, the exercise rate significantly increases. As the exercise rate increases the subject breathes faster. Faster breathing shortens the breathing cycle, and in particular, the expiratory part of the breathing cycle. By shortening the expiratory part of the breathing cycle less time is available for the lungs to empty. Since generally, ones lungs empty exponentially the shortened expiratory part of the cycle leads to a higher intrinsic positive end-expiratory pressure which is the pressure in the breathing cycle at which expiration ends and the subject commences the inspiratory part of the breathing cycle. Breathing being under the control of the nervous system is relatively oblivious to the mechanics of the operation of the lungs and their state of emptiness during a breathing cycle. Thus, as the intrinsic positive end-expiratory pressure increases over a number of breathing cycles as a result of increase in the exercise rate, known apparatus are unable to cope with the increased exercise rate. Similar problems may arise in the case of a resting subject should an event or crisis occur which causes an increase in the breathing rate of the subject.

There is therefore a need for apparatus and a method for relieving dyspnoea in a subject which overcomes these problems.

The present invention is directed towards providing such a method and apparatus.

According to the invention there is provided apparatus for relieving dyspnoea in a subject, the apparatus comprising an air supply means for providing an air supply at a pressure greater than ambient for delivery to the subject, wherein the apparatus further comprises a monitoring means for monitoring at least a part of at least one breathing cycle of the subject for determining the intrinsic positive end-expiratory pressure of a breathing cycle of the subject, and a control means responsive to the monitoring means for controlling the pressure of the air supply delivered to the subject at a pressure substantially matched to the intrinsic positive end-expiratory pressure.

In one embodiment of the invention the control means controls the pressure of the air supply delivered to the subject at the pressure substantially matched to the intrinsic positive end-expiratory pressure for a period at least at the end of the expiratory part of each breathing cycle.

In another embodiment of the invention the control means controls the pressure of the air supply delivered to the subject at a pressure greater than the intrinsic positive end-expiratory pressure during at least a part of the inspiratory part of each breathing cycle.

In a further embodiment of the invention the control means controls the pressure of the air supply delivered to the subject at the pressure substantially matched to the intrinsic positive end-expiratory pressure during the expiratory part of each breathing cycle.

In a still further embodiment of the invention the control means controls the pressure of the air supply delivered to the subject at a pressure greater than the intrinsic positive end-expiratory pressure during the inspiratory part of each breathing cycle.

In one embodiment of the invention the monitoring means monitors a plurality of breathing cycles, and a computing means is provided for determining the average intrinsic positive end-expiratory pressure over the said plurality of breathing cycles.

In another embodiment of the invention the monitoring means monitors each breathing cycle over the complete breathing cycle.

Preferably, the monitoring means is adapted for locating adjacent the mouth of the subject.

In one embodiment of the invention the monitoring means is adapted for locating in a mouthpiece, a nasal mask or a face mask or adjacent thereto through which the air supply is delivered to the subject.

In another embodiment of the invention signals are relayed from the monitoring means to the control means.

In one embodiment of the invention the monitoring means is connected to the control means by hard wiring.

Alternatively, a means for transmitting an airborne signal from the monitoring means to the control means is provided, and a receiving means is provided in the control means for receiving the airborne signal transmitted from the monitoring means.

Preferably, the monitoring means is a pressure transducer for monitoring the pressure of air during the breathing cycles.

Advantageously, the apparatus comprises a mouthpiece, nasal mask or a face mask, and a communicating means for communicating the mouthpiece or mask with the air supply means.

In one embodiment of the invention an exhaust means is provided in the mouthpiece or mask for exhausting exhaled air from the subject, and preferably, a valving means is provided in the exhaust means of the mouthpiece or mask, the valving means being operable under the control of the control means in response to the monitoring means for controlling the pressure of the air supply in the mouthpiece.

In a still further embodiment of the invention the valving means is a pressure regulating valving means.

In another embodiment of the invention the air supply means is operable under the control of the control means in response to the monitoring means for controlling the pressure of the air supply delivered to the subject.

In one embodiment of the invention the apparatus is portable and is adapted for use by an ambulatory exercising subject.

Ideally, the apparatus comprises a housing defining a hollow interior region, the air supply means being located within the hollow interior region. Preferably, the control means is located within the hollow interior region of the housing. Advantageously, a power source is located in the hollow interior region.

In one embodiment of the invention an air inlet and an air outlet are provided to and from the hollow interior region and the air supply means is located intermediate the air inlet and the air outlet.

Preferably, a first air filtering means is located adjacent the air inlet upstream of the air supply means, and preferably, a second air filtering means is located adjacent the air outlet of the air supply means.

Advantageously, the air outlet is adapted for receiving the communicating means.

In one embodiment of the invention a strap is provided for securing the housing to the subject.

In another embodiment of the invention a retaining means is provided on the strap for retaining the mouthpiece or mask releasably secured to the strap when not required.

In a further embodiment of the invention a receiving means is provided on the strap for receiving the communicating means. Preferably, the receiving means is a releasable receiving means for releasably receiving the communicating means.

In a further embodiment of the invention the communicating means comprises an elongated communicating conduit.

Advantageously, the communicating means comprises an elongated flexible communicating conduit.

Ideally, the communicating conduit is of concertina type construction for facilitating flexing of the conduit and storing of the conduit.

In another embodiment of the invention the control means comprises the computing means.

In a further embodiment of the invention the air supply means comprises an air blower motor. Preferably, the air blower motor is electrically powered. Advantageously, the air blower motor comprises an impeller driven by a motor.

In one embodiment of the invention the pressure at which the air supply is delivered to the subject when the pressure of the air supply is matched to the intrinsic positive end-expiratory pressure is substantially similar to the intrinsic positive end-expiratory pressure of the subject monitored by the monitoring means.

Additionally the invention provides a method for relieving dyspnoea in a subject, the method comprising the steps of providing an air supply means for delivering an air supply to the subject at a pressure greater than ambient, wherein the method further comprises monitoring at least a part of at least one breathing cycle of the subject for determining the intrinsic positive end-expiratory pressure of the subject, and controlling the pressure of the air supply to the subject so that the pressure of the air supply delivered to the subject is substantially matched to the intrinsic positive end-expiratory pressure.

In one embodiment of the invention the pressure of the air supply delivered to the subject is controlled at the pressure substantially matched to the intrinsic positive end-expiratory pressure for a period at least at the end of the expiratory part of each breathing cycle.

In another embodiment of the invention the pressure of the air supply delivered to the subject is controlled at a pressure greater than the intrinsic positive end-expiratory pressure during at least a part of the inspiratory part of each breathing cycle.

In a further embodiment of the invention the pressure of the air supply delivered to the subject is controlled at the pressure substantially matched to the intrinsic positive end-expiratory pressure during the expiratory part of each breathing cycle.

In a still further embodiment of the invention the pressure of the air supply delivered to the subject is controlled at a pressure greater than the intrinsic positive end-expiratory pressure during the inspiratory part of each breathing cycle.

In one embodiment of the invention a plurality of breathing cycles of the subject are monitored for determining the average intrinsic positive end-expiratory pressure over the said plurality of breathing cycles.

In another embodiment of the invention the complete breathing cycle of each monitored breathing cycle is monitored.

Preferably, the air pressure adjacent the mouth of the subject is monitored for determining the intrinsic positive end-expiratory pressure.

Advantageously, the air pressure is monitored in a mouthpiece, nasal mask or a face mask attached to the subject for determining the intrinsic positive end-expiratory pressure.

In one embodiment of the invention the pressure at which the air supply is delivered to the subject is at a pressure substantially similar to the determined intrinsic positive end-expiratory pressure.

In another embodiment of the invention the method is for relieving dyspnoea in an ambulatory exercising subject, and the method comprises the step of providing the air supply means as a portable air supply means.

The advantages of the invention are many. By virtue of the fact that the apparatus and method control the pressure at which the air supply is supplied to the subject at the end of the expiratory part of each breathing cycle so that the pressure of the air supply to the subject is matched to the intrinsic positive end-expiratory pressure of the subject, the subject can effectively commence inspiration immediately the expiratory part of the breathing cycle has ended. This permits maximum intake of air by the subject during the inspiration part of each breathing cycle. In other words, by virtue of the fact that the subject can commence inspiration immediately at the end of the expiratory part of the breathing cycle air can be drawn into the lungs of the subject over the entire inspiratory part of the breathing cycle. This, thus, maximises the volume of air drawn into the lungs of the subject during each breathing cycle. The matching of the pressure of the air supply delivered to the subject with the intrinsic positive end-expiratory pressure of the subject at the end of the expiratory part of each breathing cycle removes the threshold load which subjects typically encounter at the commencement of the inspiratory part of a breathing cycle. This threshold load which would otherwise be encountered by a subject is caused where the pressure of the air supply delivered to the subject is below the intrinsic positive end-expiratory pressure. Thus, by providing the air supply to the subject at a pressure matched to the intrinsic positive end-expiratory pressure at the end of the expiratory part of each breathing cycle the threshold load is eliminated.

In embodiments of the invention where the pressure of the air supply to the subject during part or all of the inspiratory part of each breathing cycle is greater than the intrinsic positive end-expiratory pressure, a further advantage is achieved in that a greater volume of air can be drawn into the lungs of the subject during the inspiratory part of the cycle.

Figure 1:
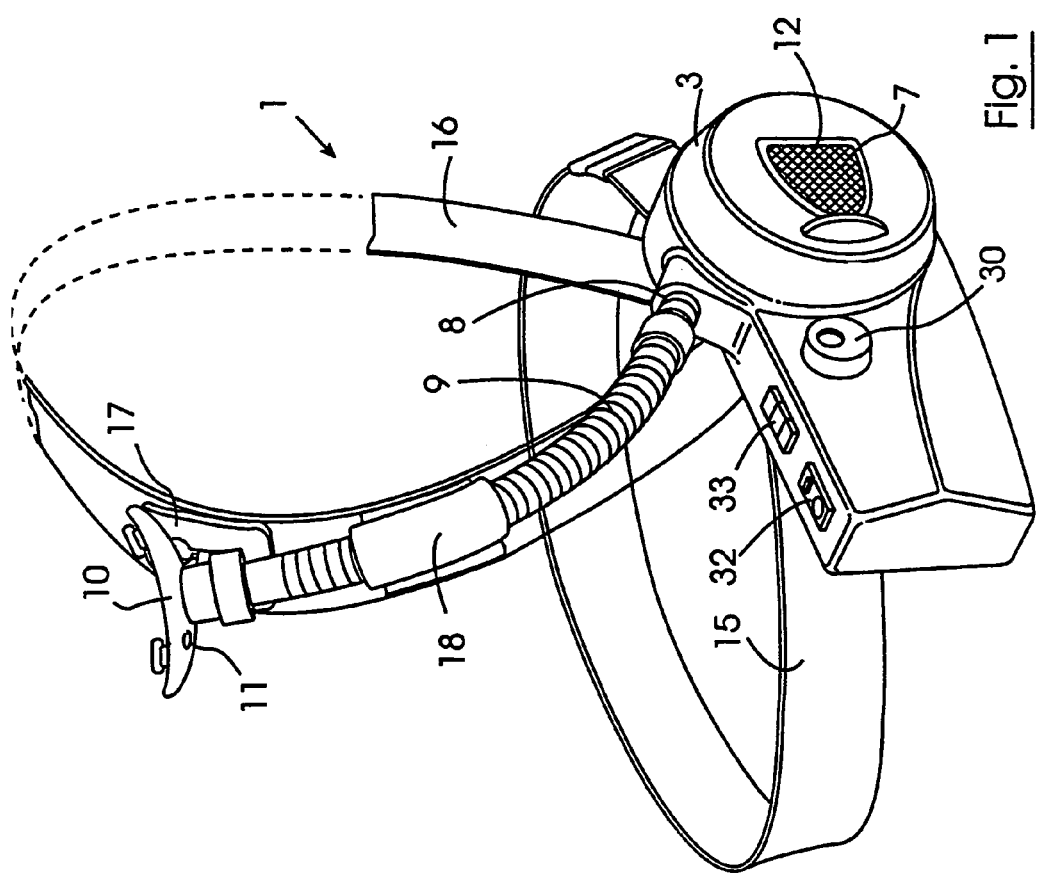
Figure 4:
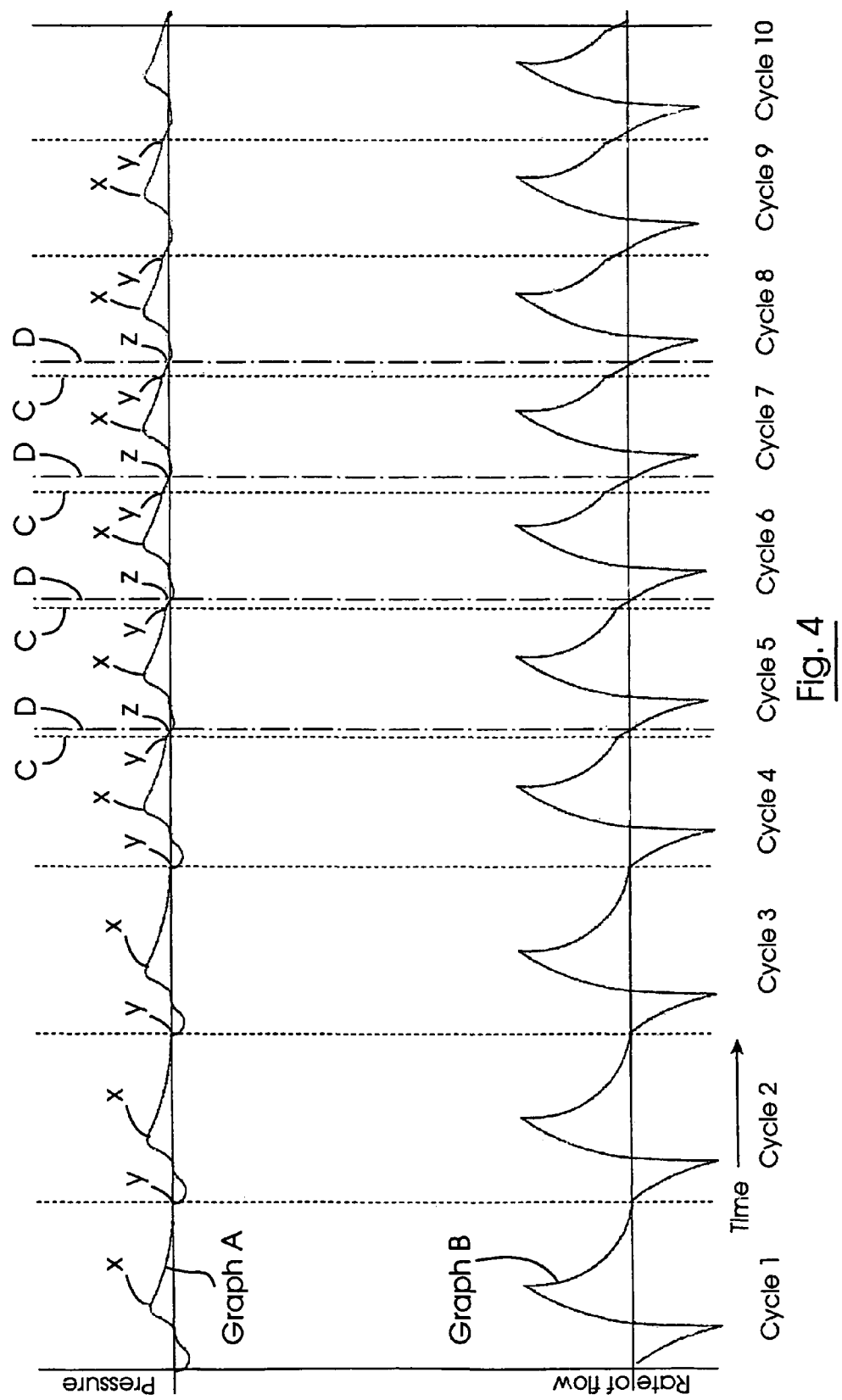
Figure 5:
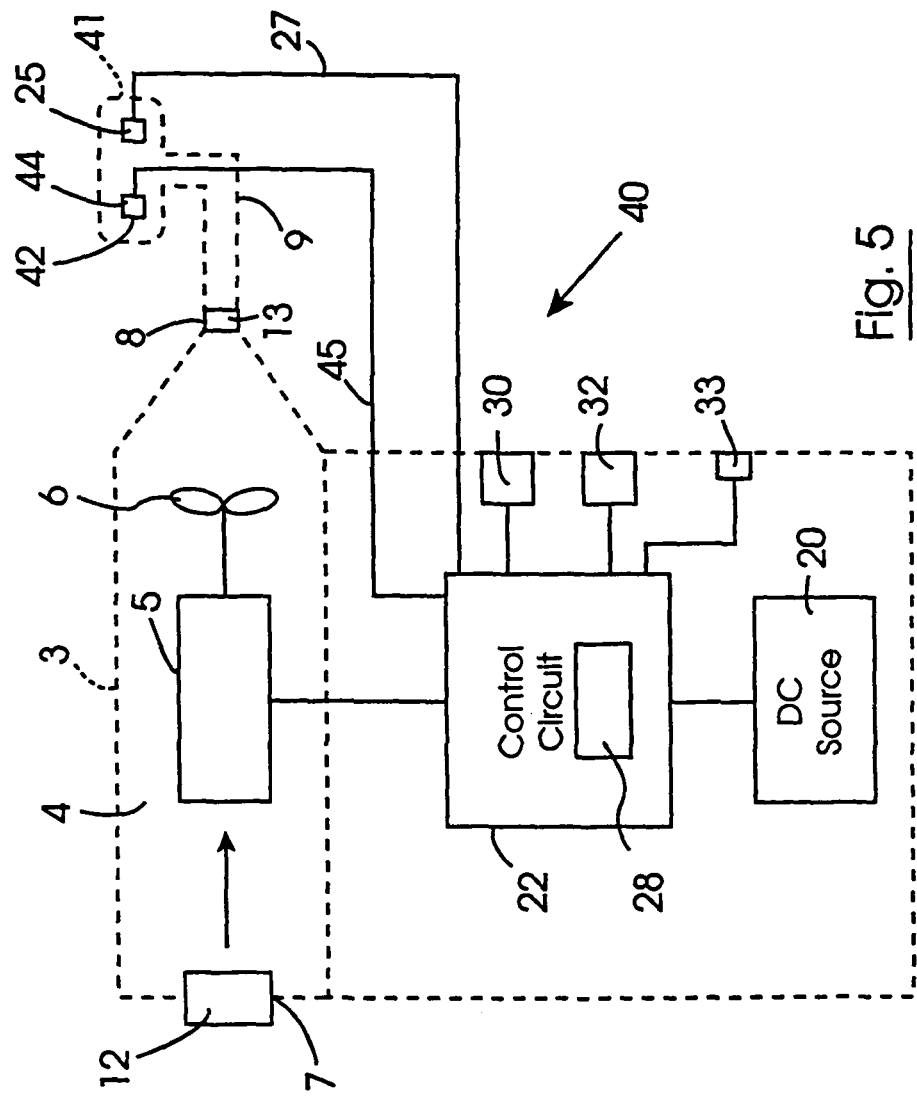

The invention will be more clearly understood from the following description of some preferred embodiments thereof which are given by way of example only with reference to the accompanying drawings, in which:

FIG. 1 is a perspective view of apparatus according to the invention for relieving dyspnoea in an ambulatory exercising subject, FIG. 2 is a perspective view of the apparatus of FIG. 1 in use, FIG. 3 is a block representation of a circuit of the apparatus of FIG. 1, FIG. 4 illustrates graphs of a number of consecutive breathing cycles of an ambulatory subject during exercising, FIG. 5 is a view similar to FIG. 3 of apparatus according to another embodiment of the invention for relieving dyspnoea in an ambulatory exercising subject, and FIG. 6 is a side elevational view of a portion of the apparatus of FIG. 5.

Referring to the drawings and initially to FIGS. 1 to 4 there is illustrated apparatus according to the invention indicated generally by the reference numeral 1 for relieving dyspnoea in a subject, and in this embodiment of the invention in an ambulatory exercising subject. The apparatus 1 is portable and is suitable for wearing by the subject as illustrated in FIG. 2. The apparatus 1 comprises a housing 3 which defines a hollow interior region 4. An air supply means, namely, a variable speed air blower motor 5 having an impeller 6 is located within the hollow interior region 4 for delivering an air supply to the subject at a pressure greater than ambient pressure as will be described below. An air inlet port 7 in the housing 3 accommodates air into the hollow interior region 4 to be blown by the air blower motor 5 and the impeller 6 through an outlet port 8 for delivery to the subject.

A communicating means, namely, a communicating conduit 9 of flexible plastics material communicates the outlet port 8 with a mouthpiece 10 to which the air supply is delivered to the subject. The communicating conduit 9 is of concertina construction for facilitating flexing of the conduit 9 and storing thereof. An exhaust means, namely, an exhaust port 11 in the mouthpiece 10 assists in exhausting expired air from the subject. A first air filtering means provided by a first air filter 12 located in the air inlet port 7 filters air to the air blower motor and the impeller 6, while a second air filtering means, namely, a second air filter 13 is located in the air outlet port 8 for filtering the air supply to the subject, and also for filtering expired air which may flow back through the conduit 9. A waist strap 15 and a shoulder strap 16 secured to the housing 3 releasably secure the housing 3 to the subject. A retaining means, namely, a retaining clip 17 is provided on the shoulder strap 16 for releasably retaining the mouthpiece 10 on the shoulder strap 16 when not in use. A receiving means, namely, a receiving clip 18 on the shoulder strap 16 releasably receives and secures the communicating conduit 9 to the shoulder strap 16.

A power supply means, namely, a DC power source provided by a battery 20 is located in the housing 3 for powering the air blower motor 5. The speed of the blower motor 5 is controlled by a control means, namely, a control circuit 22 for varying the flow rate of the air supply to the subject, for in turn varying the pressure at which the air supply is delivered to the subject.

A monitoring means, in this embodiment of the invention provided by a pressure transducer 25 is located in the mouth piece 10 for monitoring air pressure in the mouth piece 10 during a plurality of complete breathing cycles so that the average intrinsic positive end-expiratory pressure of the subject may be determined.

Referring in particular to FIG. 4, the intrinsic pressure and flow rate of air during the inspiratory part and the expiratory part of a breathing cycle of an ambulatory exercising subject during ten typical breathing cycles is illustrated. It should be noted that the graphs A and B are not to scale, and are provided solely for the purpose of illustrating typical breathing cycles. Graph A illustrates the intrinsic pressure, while graph B illustrates the intrinsic flow rate of air. During the first three breathing cycles the subject is exercising at a relatively low constant rate, for example, walking. However, during the next seven breathing cycles the exercise rate of the subject is increased, for example, by changing from walking to running, or ascending a stairs or the like. As can be seen from graph A as the exercise rate increases the breathing cycle time is reduced. In other words, the breathing cycle time for cycles four to ten is less than the breathing cycle time for the first three breathing cycles. In particular, as the breathing cycle time is reduced the time period of the expiratory part of each breathing cycle from the positive peak X to the point Y in each breathing cycle of graph A is likewise reduced. As can be seen from graph B this, thus, reduces the volume of air which can be exhaled by the subject, and in turn raises the intrinsic positive end-expiratory pressure of each breathing cycle. The intrinsic positive end-expiratory pressure of each breathing cycle is the point Y where the graph Y cuts the verticals C. In the first three breathing cycles the point Y lies on the x-axis. Thus, in the first three breathing cycles the subject can commence drawing air into his or her lungs at the very beginning of the inspiratory part of each breathing cycle, in other words, at the point Y. However, as the exercise rate increases the point Y rises above the x-axis, and thereby, although expiration has ceased at the point Y, inspiration cannot commence until the intrinsic pressure has dropped to the x-axis, in other words, until the point Z has been reached. Therefore, the subject is unable to draw air into his or her lungs during the period Y to Z of each breathing cycle, in other words, during the time period between the adjacent verticals C and D.

The apparatus as will be described below by monitoring the intrinsic pressure of the breathing cycles of the subject, and by determining the average intrinsic positive end-expiratory pressure, in other words, the average of the pressure values of the points Y over a plurality of breathing cycles, in this case, five breathing cycles, and then by increasing the pressure of the air supply to the subject to the average of the pressure values of the points Y, allows the subject to commence drawing in air immediately at the commencement of the inspiratory part of each breathing cycle. In other words, the subject can draw air into his or her lungs immediately the point Y has been reached in each breathing cycle.

The pressure transducer 25 monitors air pressure and may also monitor air flow in the mouthpiece 10. Signals from the pressure transducer 25 are relayed through hard wiring 27 to the control circuit 22. A computing means provided by a microprocessor 28 in the control circuit 22 determines the average intrinsic positive end-expiratory pressure of the subject from the signals received from the pressure transducer 25 using one or more appropriate algorithms. Typically, signals from five consecutive breathing cycles are read by the microprocessor 28, and the average intrinsic positive end-expiratory pressure of the subject is determined over the five breathing cycles. The determination of intrinsic positive end-expiratory pressure in a subject will be well known to those skilled in the art, and it is not intended to describe the algorithms in detail. The microprocessor 28 in the control circuit 22 controls the control circuit 22 for in turn controlling the air blower motor 5 for delivering the air supply at an appropriate flow rate to the mouthpiece 10 so that the air supply delivered to the mouthpiece 10 is at a pressure matched to the determined average intrinsic positive end-expiratory pressure. In this embodiment of the invention the air supply is delivered to the mouthpiece 10 at a pressure similar to the determined average intrinsic positive end-expiratory pressure. The control circuit 22 controls the air blower motor 5 for maintaining the pressure of the air supply at the appropriate pressure until signals received from the pressure transducer 25 in the mouthpiece 10 indicate that a further change in the average intrinsic positive end-expiratory pressure has occurred. At which stage the control circuit 22 again controls the blower motor 5 to again match the pressure of the air supply to the newly determined average intrinsic positive end-expiratory pressure.

A control knob 30 located exteriorly on the housing 3 is operably connected to the control circuit 22 for providing manual control of the control circuit 22 for in turn manually controlling the pressure at which the air blower motor 5 delivers the air supply to the mouth piece 10, should the subject decide to control the air supply pressure manually. A button switch 32 also located exteriorly on the housing 3 is operably connected to the control circuit 2 for facilitating selection by the subject between an automatic operation mode of the apparatus 1 and a manual operation mode of the apparatus 1. When the apparatus 1 is operated in the manual mode the pressure at which the air supply is delivered to the mouth piece 10 is controlled by the control knob 30, and when the apparatus 1 is operated in the automatic mode the pressure at which the air supply is delivered to the mouth piece 10 is determined by the control circuit 22 from signals received from the pressure transducer 25 in the mouth piece 10. An indicator light 33 on the housing 3 indicates when the apparatus 1 is operating in the automatic mode.

In use, a subject wears the apparatus 1 as illustrated in FIG. 2, and when a supply of air at a pressure greater than ambient is required the subject breaths through the mouth piece 10. If it is desired to operate the apparatus 1 in the manual operating mode, the button switch 32 is depressed and the control knob 30 is rotated until the air supply to the subject is at the desired pressure. When it is desired to operate the apparatus 1 in the automatic operating mode the button switch 32 is again depressed switching the apparatus 1 to operate in the automatic mode. In this mode, signals from the pressure transducer 25 are read by the microprocessor 28 in the control circuit 22 which continuously determines the average intrinsic positive end-expiratory pressure. The control circuit 22 sets the speed of the blower motor 5 at an appropriate speed to deliver the air supply at a flow rate so that the pressure of the air supply delivered to the mouthpiece 10 is similar to the determined average intrinsic positive end-expiratory pressure. The pressure transducer 25 continues to monitor the intrinsic pressure of the breathing cycles of the subject, and the microprocessor 28 continuously determines the average intrinsic positive end-expiratory pressure from the signals received from the pressure transducer 25. On a change in the average intrinsic positive end-expiratory pressure being determined the control circuit 22 resets the speed of the blower motor 5 for delivering the air supply at the appropriate flow rate so that the pressure of the air supply in the mouthpiece 10 is matched to the new average intrinsic positive end-expiratory pressure, and so operation of the apparatus 1 continues.

Referring now to FIGS. 5 and 6 there is illustrated apparatus according to another embodiment of the invention indicated generally by the reference numeral 40 also for relieving dyspnoea in an ambulatory exercising subject. The apparatus 40 is substantially similar to the apparatus 1 and similar components are identified by the same reference numerals. The main difference between the apparatus 40 and the apparatus 1 is that the blower motor 5 is a constant speed motor, and thus, delivers the air supply at a constant pressure. In this embodiment of the invention the air supply is provided to the subject through a mouth and nasal mask 41 within which the pressure transducer 25 is located. An exhaust means provided by an exhaust port 42 from the mouth and nasal mask 41 exhausts expired air from the subject. A valving means, in this embodiment of the invention a variable pressure regulating valve 44 is located in the exhaust port 42 for controlling the pressure of the air supply in the mouth and nasal mask 41. The valve 44 is hard wired to the control circuit 22 by a cable 45, and the control circuit 22 controls the valve 44 for maintaining the pressure in the mouth and nasal mask 41 at a pressure similar to the average intrinsic positive end-expiratory pressure determined by the microprocessor 28 in response to signals received from the pressure transducer 25. In this embodiment of the invention the only control exercised over the air blower motor 5 by the control circuit 22 is to switch on and off the air blower motor 5 as the apparatus 40 is required to deliver an air supply to the subject.

Operation of the apparatus 40 is substantially similar to that of the apparatus 1. The average intrinsic positive end-expiratory pressure of the subject is determined by the microprocessor 28 of the control circuit 22 from signals read from the pressure transducer 25. On determining the average intrinsic positive end-expiratory pressure, the control circuit 22 then sets the valve 44 appropriately so that the air supply in the mouth and nasal mask 41 is at a pressure similar to the average intrinsic positive end-expiratory pressure determined by the microprocessor 28. On the microprocessor 28 determining a change in the average intrinsic positive end-expiratory pressure, the control circuit 22 resets the valve 44 appropriately, so that the air supply in the mask 41 is again at a pressure similar to the new average intrinsic positive end-expiratory pressure, and so operation of the apparatus 40 continues. Otherwise, operation of the apparatus 40 is similar to that of the apparatus 1.

It is envisaged that the microprocessor 28 of the apparatus 1 and the apparatus 40 may be programmed so that the air supply is delivered to the subject at a pressure similar to the average intrinsic positive end-expiratory pressure during the expiratory part of each breathing cycle, and just after the commencement of the inspiratory part of each breathing cycle, the pressure of the air supply to the subject would be raised to a pressure greater than the average intrinsic positive end-expiratory pressure, and the pressure of the air supply to the subject would be maintained at that greater pressure until the end of the inspiratory part of each breathing cycle, at which stage the pressure of the air supply would be reduced to the average intrinsic positive end-expiratory pressure. This would facilitate inspiration by the subject so that the subject could draw in a greater volume of air during the inspiratory part of the breathing cycle. At the end of the inspiratory part of each breathing cycle the air blower motor or the valve 44 would be operated to deliver the air supply to the subject at a pressure similar to the average intrinsic positive end-expiratory pressure until the expiratory part of each breathing cycle had been completed. Should the microprocessor be programmed in this way the microprocessor would determine the beginning and end of the respective expiratory and inspiratory parts of the breathing cycle by reading the signals from the pressure transducer 25.

It is envisaged that an oxygen supply may be provided in the housing for mixing with the air supply being delivered to the subject. In the event of an oxygen supply being provided, the control circuit would control the supply of oxygen into the air supply so that the pressure at which the oxygen is being delivered to the subject is similar to pressure at which the air supply is being delivered.

While the air supply is described as being delivered to the subject through a mouthpiece or mouth and nasal mask, the air supply may be delivered to the subject through any other suitable means, for example, a nasal mask, a face mask or the like.

It will be appreciated that while the air supply means has been described as comprising a blower motor and impeller, any other suitable air supply means may be provided, for example, an air compressor, a diaphragm pump, a piston pump of an appropriate size and with an adequate dynamic response.

While the pressure transducer has been described as being hard wired to the control circuit, it will be appreciated that signals from the pressure transducer may be relayed to the control circuit by radio waves from a radio transmitter located adjacent the pressure transducer to a radio receiver located in the control circuit. Needless to say, any other airborne communicating waves may be used for relaying signals from the pressure transducer to the control circuit.

While the monitoring means has been described as being a pressure transducer located adjacent the mouth of the subject, the monitoring means may be provided by a pressure transducer located in the housing downstream of the air supply means. In which case a flow meter would be provided for measuring the flow rate of the air supply from the air supply means, and knowing the resistance of the communicating means the intrinsic pressure during each breathing cycle of the subject could be determined from signals read from the pressure transducer and the flow meter.

While the average intrinsic positive end-expiratory pressure has been described as being determined over five breathing cycles, the average intrinsic positive end-expiratory pressure may be determined over any other suitable number of breathing cycles. Furthermore, in certain cases it is envisaged that instead of determining the average intrinsic positive end-expiratory pressure, intrinsic positive end-expiratory pressure may be used directly.

The invention claimed is:

1. An apparatus for providing pressure support to a subject, the apparatus comprising:
   a gas flow generating system adapted to provide a flow of gas;
   a monitor configured to monitor intrinsic positive end-expiratory pressure of breathing cycles of the subject; and
   a controller configured to, at the end of the expiratory part of a breathing cycle, control the gas flow generating system to match a pressure of the flow of gas to the subject an average of the monitored intrinsic positive end-expiratory pressure,
   wherein the matched pressure of the flow of gas delivered to the subject allows the subject to commence drawing in the gas immediately at commencement of the inspiratory part of the breathing cycle.

2. The apparatus as claimed in claim 1, wherein the controller is configured to control the gas flow generating system such that the pressure of the flow of gas delivered to the subject during the inspiratory phase of the breathing cycle is at a pressure greater than the average of the monitored intrinsic positive end-expiratory pressure.

3. The apparatus as claimed in claim 1, wherein the gas flow generating system includes a blower motor, and wherein the controller is configured to control the pressure provided by the gas flow generating system by controlling an operating speed of the blower motor.

4. The apparatus as claimed in claim 1, wherein the monitor is located proximate to an airway of the subject.

5. The apparatus as claimed in claim 4, further comprising:
   a patient circuit having a first end operatively connected to the gas flow generating system and a second end; and
   a patient interface operatively connected to the second end of the patient circuit, and wherein the monitor is operatively connected to the patient interface.

6. The apparatus as claimed in claim 1, wherein the monitor is connected to the controller by a wire.

7. The apparatus as claimed in claim 1, wherein the monitor includes a transmitter configured to transmit a wireless signal to the controller, and wherein the controller includes a receiver configured to receive the wireless signal.

8. The apparatus as claimed in claim 1, wherein the monitor is a pressure transducer.

9. The apparatus as claimed in claim 1, wherein the apparatus is portable and is adapted for use by ambulatory subject.

10. The apparatus as claimed in claim 1, wherein the gas flow generating system comprises an electrically powered blower motor.

11. A method for relieving dyspnoea in a subject, the method comprising acts of:
    delivering a flow of gas to an airway of the subject at a pressure greater than ambient;
    monitoring intrinsic positive end-expiratory pressure of a plurality of breathing cycles of the subject; and
    matching, at the end of the expiratory part of the plurality of breathing cycles, the pressure of the flow of gas delivered to the subject to an average of the monitored intrinsic positive end-expiratory pressure,
    wherein the matched pressure of the flow of gas delivered to the subject allows the subject to commence drawing in the gas immediately at commencement of the inspiratory part of the breathing cycle.

\* \* \* \* \*